United States Patent [19]
Collins et al.

[11] Patent Number: 5,925,559
[45] Date of Patent: Jul. 20, 1999

[54] PHAGEMIDS AND PROCESS OF PREPARATION

[75] Inventors: John Collins; Peter Roettgen, both of Braunschweig, Germany

[73] Assignee: Gesellschaft fur Biotechnologische Forschung GmbH, Brunswick, Germany

[21] Appl. No.: 08/880,829

[22] Filed: Jun. 23, 1997

Related U.S. Application Data

[63] Continuation of application No. 08/458,669, Jun. 2, 1995, abandoned.

[30] Foreign Application Priority Data

Jun. 7, 1994 [EP] European Pat. Off. .............. 94108689

[51] Int. Cl.$^6$ .............................. C12P 21/02; C12N 1/21; C12N 7/01
[52] U.S. Cl. .................................... 435/252.33; 435/69.1; 435/69.2; 435/69.7; 435/235.1; 435/257.3
[58] Field of Search ........................... 435/252.33, 257.3, 435/69.1, 69.2, 213, 218, 235.1, 69.7; 536/23.1, 23.2; 935/22, 31, 59, 66, 73

[56] References Cited

U.S. PATENT DOCUMENTS

| | | | |
|---|---|---|---|
| 5,223,409 | 6/1993 | Ladner et al. | 435/69.7 |
| 5,395,750 | 3/1995 | Dillon et al. | 435/5 |
| 5,403,484 | 4/1995 | Ladner et al. | 435/235.1 |

OTHER PUBLICATIONS

Roberts et al "Directed Evolution of a Protein . . ." Proc. Natl. Acad. Sci. 89: 2429–2433 1992.
Markland et al. "Design, Construction & Function of a Multicopy Display Vector Using Fusions . . . " Gene 109:13–19 1991.
Hogrefe et al "A Bacteriophage Lambda Vector For The Cloning and & Expression of Immunoglobulin Fab Fragments . . . " Gene 128:119–126 1993.
Pannekoek et al. "Functional Display of Human Plasminogen–Activator Inhibitor–1 (PAI) . . . "Gene 128 135–140 1993.
Breitling et al. "A surface Expression Vector for Antibody Screening" Gene 104: 147–153 1991.
Dennis et al. "Kunitz Domain Inhibitors of Tissue Factor–Factor VIIa" J Biol Chem. 269(35):22129–22136 1994.
Marks et al. "By–Passing Immunization" J Mol. Biol. 222:581–597 1991.
Kang et al. "Linkage of Recognition & Replication Functions . . . " Proc. Natl. Acad. Sci. 88:4363–4366 1991.
Clackson et al. "Making Antibody Fragments Using Phage Display Libraries" Nature 352:624–628 1991.
Kay et al. "An M13 Phage Library Displaying Random 38–amino–Acid Peptides . . . " Gene 128:59–65 1993.
Tsunetsugu–Yokota et al. "Expression of An Immunogenic Region of HIV by A Filamentous Bacteriophage Vector" Gene 99 261–265 1991.
Lowman et al. "Selecting High Affinity Binding Proteins by Monovalent Phage Display" Biochemistry 30:10832–10838, 1991.
Bass et al. "Hormone Phage: An Enrichment Method for Variant Proteins w/ Altered Binding Properties" Prot. Struct. Funct. Genet. 8:309–314 1990.
Corey et al. "Trypsin Display on The Surface of Bacteriophage" Gene 128 129–134 1993.
Willis et al. "Immunological Properties of Foreign Peptides In Multiple Display . . . " Gene 128 79–83 1993.
Makowski et al. "Structural Constraints On The Display of Foreign Peptides on Filamentous Bacteriophages" Gene 128 5–11 1993.
Matthews et al. "Substrate Phage: Selection of Protease Substrates by Monovalent Phage Display" Science 260:1113–1117 1993.
Devlin et al. "Random Peptide Libraries: A Source of Specific Protein Binding Molecules" Science 249 404–406 1990.
Yankovsky et al "Phasmids As Effective & Simple Tools For Construction & Analysis of Gene Libraries" Gene 81 203–210 1989.
Szardenings et al "A Phasmid Optimized For Protein Design Projects: PMAMPP" Gene 94 1–7 1990.

*Primary Examiner*—Nancy Degen
*Attorney, Agent, or Firm*—Kane, Dalsimer, Sullivan, Kurucz, Levy, Eisele and Richard, LLP

[57] ABSTRACT

The invention concerns a collection of phagemids made up of a promotor, a gene of a fusion between a ligand protein, wherein the ligand protein in its processed state would be of from 40 to 60 amino acid residues, and a bacteriophage protein, at least one transcription terminator sequence, a replication origin derived from a single strand bacteriophage, a plasmid replication origin and facultatively at least one selection marker. Further, the invention concerns a collection of *Escherichia coli* clones or cells representing the collection of phagemids, a process for isolating phagemid particles with strong binding characteristics for a defined target molecule with the use of collections according to the invention and phagemid particles obtained according to the process.

10 Claims, 7 Drawing Sheets

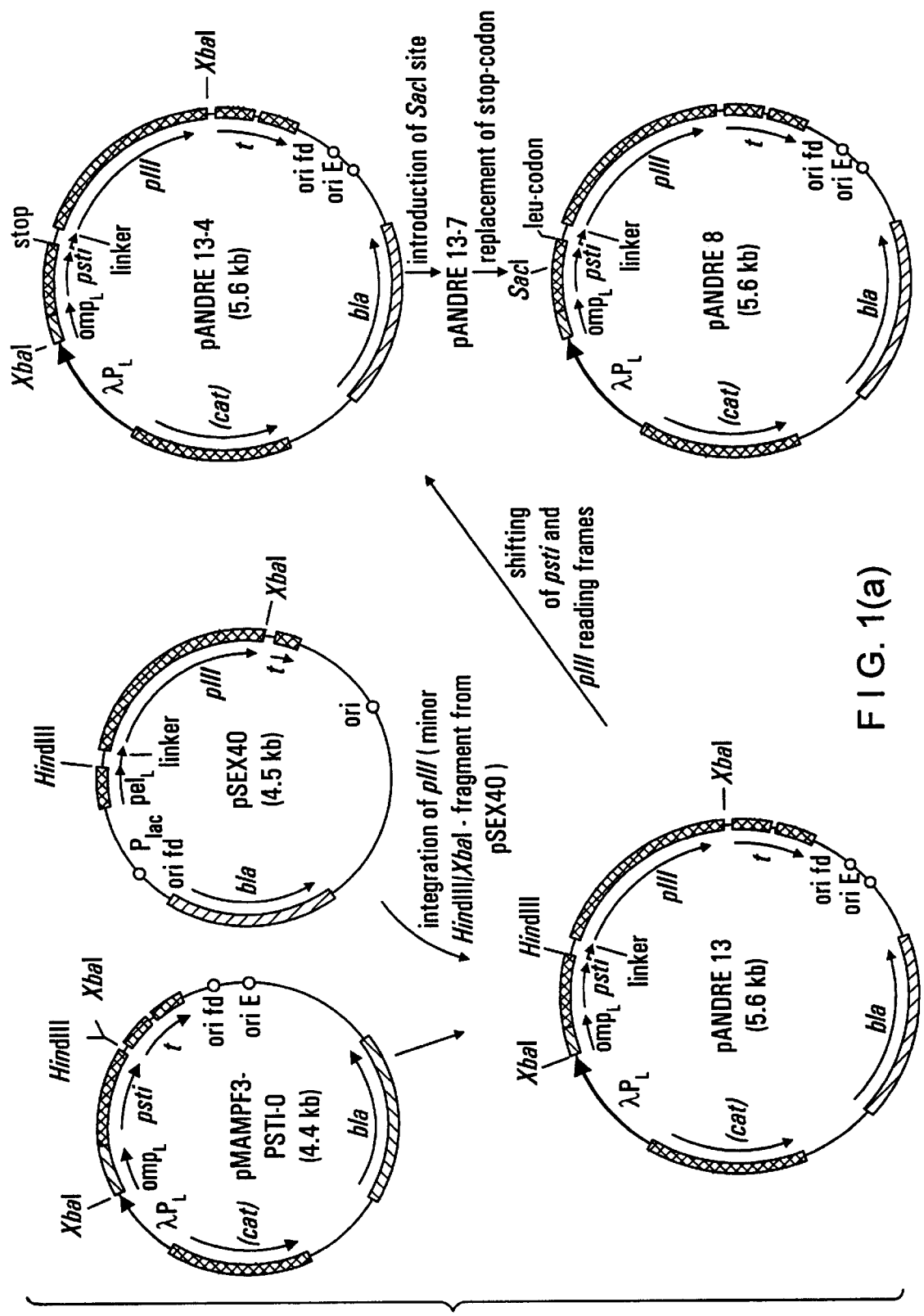
F I G. 1(a)

```
pANDRE 13      C  Y  N  E  L  N  G  C ...           ← psti →         K  S  G  P  C  *           L  E  E  G  E  F
               TGCTACAACGAACTGAACGGTTGC...                            AAATCTGGTCCGTGCTGAATTCA AGCTTGAAGAAGGTGAATTC
               ACGATGTTGCTTGACTTGCCAACG...                            TTTAGACCAGGCACGACTTAAGTTCGA ACTTCTTCCACTTAAC
                                                                                              HindIII
                    25                                                        154                              192
                                              ← linker → pANDRE 13-4    C  Y  N  E  L  N  G  C ...                     ... K  S  G  P  C  *             E  E  G  E  F
               TGCTACAACGAGCTCAACGGTTGC...                    ...AAATCTGGTCCGTGCTGAATTCATGAAGAAGGTGAATTC
               ACGATGTTGCTCGAGTTGCCAACG...                    ...TTTAGACCAGGCACGACTTAAGTACTTCTTCCACTTAAC
                    SacI
                    48                                                        154                          188 pANDRE 13-7    C  Y  N  E  L  N  G  C ...                     ... K  S  G  P  C  *             E  E  G  E  F
               TGCTACAACGAGCTCAACGGTTGC...                    ...AAATCTGGTCCGTGCTGAATTCATGAAGAAGGTGAATTC
               ACGATGTTGCTCGAGTTGCCAACG...                    ...TTTAGACCAGGCACGACTTAAGTACTTCTTCCACTTAAC pSKAN 8                                                           K  S  G  P  C  L  I  H  E  E  G  E  F
                                                                  AAATCTGGTCCGTGCTTAATTCATGAAGAAGGTGAATTC
                                                                  TTTAGACCAGGCACGAATTAAGTACTTCTTCCACTTAAC
```

FIG. 1b

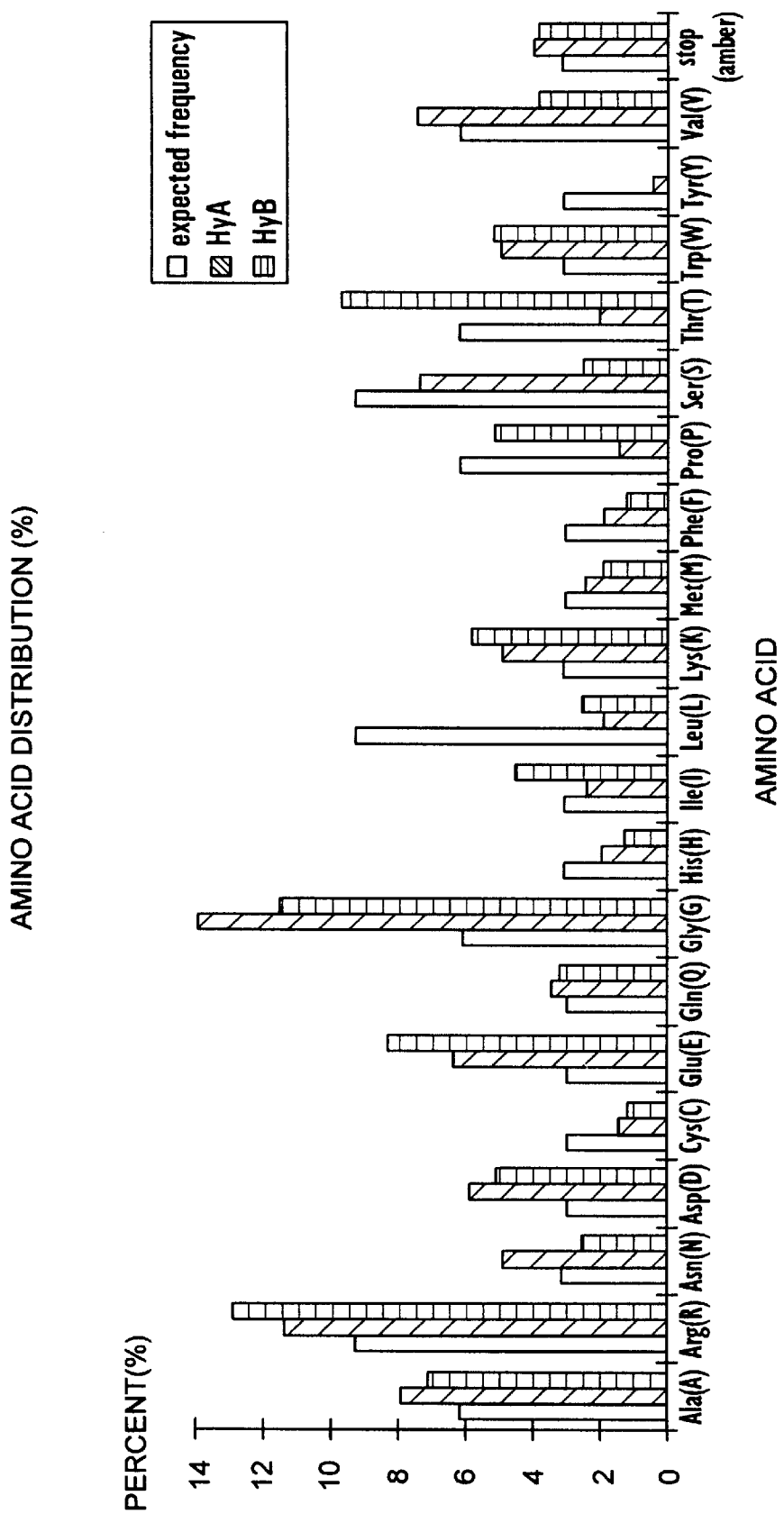
F I G. 4

SEQUENCE LISTING (1) GENERAL INFORMATION:

```
        (iii) NUMBER OF SEQUENCES: 21

(2) INFORMATION FOR SEQ ID NO: 1:

(i) SEQUENCE CHARACTERISTICS:
            (A) LENGTH:         6 base pairs
            (B) TYPE:           nucleic acid
            (C) STRANDEDNESS:   single strand
            (D) TOPOLOGY:       linear (ii) MOLECULE TYPE:

(iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (B) CLONE:

(xi) SEQUENCE DESCRIPTION: SEQ ID NO: 1:

TGAATT                                                                          6

(2) INFORMATION FOR SEQ ID NO: 2:

(i) SEQUENCE CHARACTERISTICS:
            (A) LENGTH:         6 base pairs
            (B) TYPE:           nucleic acid
            (C) STRANDEDNESS:   single strand
            (D) TOPOLOGY:       linear (ii) MOLECULE TYPE:

(iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (B) CLONE:

(xi) SEQUENCE DESCRIPTION: SEQ ID NO: 2:

TTAATT                                                                          6

(2) INFORMATION FOR SEQ ID NO: 3:

(i) SEQUENCE CHARACTERISTICS:
            (A) LENGTH:         12 base pairs
            (B) TYPE:           nucleic acid
            (C) STRANDEDNESS:   single strand
            (D) TOPOLOGY:       linear
```

```
    (ii) MOLECULE TYPE:

(iii) HYPOTHETICAL:

(iv) ANTI-SENSE:

(v) FRAGMENT TYPE:

(vi) ORIGINAL SOURCE:
         (A) ORGANISM:
         (B) STRAIN:
         (C) INDIVIDUAL ISOLATE:
         (D) DEVELOPMENTAL STAGE:
         (E) HAPLOTYPE:
         (F) TISSUE TYPE:
         (G) CELL TYPE:
         (H) CELL LINE:
         (I) ORGANELLE:

(vii) IMMEDIATE SOURCE:
         (B) CLONE:

(xi) SEQUENCE DESCRIPTION: SEQ ID NO: 3:

AACGAACTGA AC                                                                    12

(2) INFORMATION FOR SEQ ID NO: 4:

(i) SEQUENCE CHARACTERISTICS:
         (A) LENGTH:            12 base pairs
         (B) TYPE:              nucleic acid
         (C) STRANDEDNESS:      single strand
         (D) TOPOLOGY:          linear (ii) MOLECULE TYPE:

(iii) HYPOTHETICAL:

(iv) ANTI-SENSE:

(v) FRAGMENT TYPE:

(vi) ORIGINAL SOURCE:
         (A) ORGANISM:
         (B) STRAIN:
         (C) INDIVIDUAL ISOLATE:
         (D) DEVELOPMENTAL STAGE:
         (E) HAPLOTYPE:
         (F) TISSUE TYPE:
         (G) CELL TYPE:
         (H) CELL LINE:
         (I) ORGANELLE:

(vii) IMMEDIATE SOURCE:
         (B) CLONE:

(xi) SEQUENCE DESCRIPTION: SEQ ID NO: 4:

AACGAGCTCA AC                                                                    12

(2) INFORMATION FOR SEQ ID NO: 5:

(i) SEQUENCE CHARACTERISTICS:
         (A) LENGTH:            37 base pairs
         (B) TYPE:              nucleic acid
         (C) STRANDEDNESS:      single strand
         (D) TOPOLOGY:          linear (ii) MOLECULE TYPE:

(iii) HYPOTHETICAL:

(iv) ANTI-SENSE:

(v) FRAGMENT TYPE:

(vi) ORIGINAL SOURCE:
```

```
             (A) ORGANISM:
             (B) STRAIN:
             (C) INDIVIDUAL ISOLATE:
             (D) DEVELOPMENTAL STAGE:
             (E) HAPLOTYPE:
             (F) TISSUE TYPE:
             (G) CELL TYPE:
             (H) CELL LINE:
             (I) ORGANELLE:

(vii) IMMEDIATE SOURCE:
             (B) CLONE:

(xi) SEQUENCE DESCRIPTION: SEQ ID NO: 5:

CTG AGA ATT CAC CTT CTT CAT GAA TTA AGC                              30

ACG GAC C                                                            37

(2) INFORMATION FOR SEQ ID NO: 6:

(i) SEQUENCE CHARACTERISTICS:
             (A) LENGTH:         19 base pairs
             (B) TYPE:           nucleic acid
             (C) STRANDEDNESS:   single strand
             (D) TOPOLOGY:       linear (ii) MOLECULE TYPE:

(iii) HYPOTHETICAL:

(iv) ANTI-SENSE:

(v) FRAGMENT TYPE:

(vi) ORIGINAL SOURCE:
             (A) ORGANISM:
             (B) STRAIN:
             (C) INDIVIDUAL ISOLATE:
             (D) DEVELOPMENTAL STAGE:
             (E) HAPLOTYPE:
             (F) TISSUE TYPE:
             (G) CELL TYPE:
             (H) CELL LINE:
             (I) ORGANELLE:

(vii) IMMEDIATE SOURCE:
             (B) CLONE:

(xi) SEQUENCE DESCRIPTION: SEQ ID NO: 6:

CAT GAA TTC CGC ACG GAC C                                            19

(2) INFORMATION FOR SEQ ID NO: 7:

(i) SEQUENCE CHARACTERISTICS:
             (A) LENGTH:         19 base pairs
             (B) TYPE:           nucleic acid
             (C) STRANDEDNESS:   single strand
             (D) TOPOLOGY:       linear (ii) MOLECULE TYPE:

(iii) HYPOTHETICAL:

(iv) ANTI-SENSE:

(v) FRAGMENT TYPE:

(vi) ORIGINAL SOURCE:
             (A) ORGANISM:
             (B) STRAIN:
             (C) INDIVIDUAL ISOLATE:
             (D) DEVELOPMENTAL STAGE:
             (E) HAPLOTYPE:
             (F) TISSUE TYPE:
             (G) CELL TYPE:
             (H) CELL LINE:
```

(I) ORGANELLE:

(vii) IMMEDIATE SOURCE:
                    (B) CLONE:

(xi) SEQUENCE DESCRIPTION: SEQ ID NO: 7:

GGT CCG TGC GGA ATT CAT G                                              19

(2) INFORMATION FOR SEQ ID NO: 8:

(i) SEQUENCE CHARACTERISTICS:
                    (A) LENGTH:         32 base pairs
                    (B) TYPE:           nucleic acid
                    (C) STRANDEDNESS:   single strand
                    (D) TOPOLOGY:       linear (ii) MOLECULE TYPE:

(iii) HYPOTHETICAL:

(iv) ANTI-SENSE:

(v) FRAGMENT TYPE:

(vi) ORIGINAL SOURCE:
                    (A) ORGANISM:
                    (B) STRAIN:
                    (C) INDIVIDUAL ISOLATE:
                    (D) DEVELOPMENTAL STAGE:
                    (E) HAPLOTYPE:
                    (F) TISSUE TYPE:
                    (G) CELL TYPE:
                    (H) CELL LINE:
                    (I) ORGANELLE:

(vii) IMMEDIATE SOURCE:
                    (B) CLONE:

(xi) SEQUENCE DESCRIPTION: SEQ ID NO: 8:

CCG TTG AGC TCG TTG TAG CAT TTA GCT TCA CG                             32

(2) INFORMATION FOR SEQ ID NO: 9:

(i) SEQUENCE CHARACTERISTICS:
                    (A) LENGTH:         22 base pairs
                    (B) TYPE:           nucleic acid
                    (C) STRANDEDNESS:   single strand
                    (D) TOPOLOGY:       linear (ii) MOLECULE TYPE:

(iii) HYPOTHETICAL:

(iv) ANTI-SENSE:

(v) FRAGMENT TYPE:

(vi) ORIGINAL SOURCE:
                    (A) ORGANISM:
                    (B) STRAIN:
                    (C) INDIVIDUAL ISOLATE:
                    (D) DEVELOPMENTAL STAGE:
                    (E) HAPLOTYPE:
                    (F) TISSUE TYPE:
                    (G) CELL TYPE:
                    (H) CELL LINE:
                    (I) ORGANELLE:

(vii) IMMEDIATE SOURCE:
                    (B) CLONE:

(xi) SEQUENCE DESCRIPTION: SEQ ID NO: 9:

GCA TTG GAA TTC TAC AAC TTG C                                          22

```
(2) INFORMATION FOR SEQ ID NO: 10:

(i) SEQUENCE CHARACTERISTICS:
        (A) LENGTH:          18 base pairs
        (B) TYPE:            nucleic acid
        (C) STRANDEDNESS:    single strand
        (D) TOPOLOGY:        linear (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (B) CLONE:

(xi) SEQUENCE DESCRIPTION: SEQ ID NO: 10:

GGG ATT TTG CTA AAC AAC                                              18

(2) INFORMATION FOR SEQ ID NO: 11:

(i) SEQUENCE CHARACTERISTICS:
        (A) LENGTH:          23 base pairs
        (B) TYPE:            nucleic acid
        (C) STRANDEDNESS:    single strand
        (D) TOPOLOGY:        linear (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (B) CLONE:

(xi) SEQUENCE DESCRIPTION: SEQ ID NO: 11:

GCT ACA ACG AGC TCA ACG GTT GC                                       23

(2) INFORMATION FOR SEQ ID NO: 12:

(i) SEQUENCE CHARACTERISTICS:
        (A) LENGTH:          73 base pairs
        (B) TYPE:            nucleic acid
        (C) STRANDEDNESS:    single strand
        (D) TOPOLOGY:        linear (ii) MOLECULE TYPE:
```

(iii) HYPOTHETICAL:

(iv) ANTI-SENSE:

(v) FRAGMENT TYPE:

(vi) ORIGINAL SOURCE:
              (A) ORGANISM:
              (B) STRAIN:
              (C) INDIVIDUAL ISOLATE:
              (D) DEVELOPMENTAL STAGE:
              (E) HAPLOTYPE:
              (F) TISSUE TYPE:
              (G) CELL TYPE:
              (H) CELL LINE:
              (I) ORGANELLE:

(vii) IMMEDIATE SOURCE:

(xi) SEQUENCE DESCRIPTION: SEQ ID NO: 12:

GCT ACA ACG AGC TCA ACG GTT GCN NKN NKN                                    30

NKN NKN NKN NKN NKN NKT GCG GTA CCG ACG                                    60

GTG ACA CTT ACC C                                                          73

(2) INFORMATION FOR SEQ ID NO: 13:

(i) SEQUENCE CHARACTERISTICS:
              (A) LENGTH:       70 base pairs
              (B) TYPE:         nucleic acid
              (C) STRANDEDNESS: single strand
              (D) TOPOLOGY:     linear (ii) MOLECULE TYPE:

(iii) HYPOTHETICAL:

(iv) ANTI-SENSE:

(v) FRAGMENT TYPE:

(vi) ORIGINAL SOURCE:
              (A) ORGANISM:
              (B) STRAIN:
              (C) INDIVIDUAL ISOLATE:
              (D) DEVELOPMENTAL STAGE:
              (E) HAPLOTYPE:
              (F) TISSUE TYPE:
              (G) CELL TYPE:
              (H) CELL LINE:
              (I) ORGANELLE:

(vii) IMMEDIATE SOURCE:

(xi) SEQUENCE DESCRIPTION: SEQ ID NO: 13:

GCT ACA ACG AGC TCA ACG GTT GCN NKN NKN                                    30

NKN NKN NKN NKN NKT GCG GTA CCG ACG GTG                                    60

ACA CTT ACC C                                                              70

(2) INFORMATION FOR SEQ ID NO: 14:

(i) SEQUENCE CHARACTERISTICS:
              (A) LENGTH:       70 base pairs
              (B) TYPE:         nucleic acid
              (C) STRANDEDNESS: single strand
              (D) TOPOLOGY:     linear (ii) MOLECULE TYPE:

(iii) HYPOTHETICAL:

(iv) ANTI-SENSE:

```
        (v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:

(xi) SEQUENCE DESCRIPTION: SEQ ID NO: 14:

GCT ACA ACG AGC TCA ACG GTT GCN NKN NKN                                  30

NKN NKN NKN NKN TTT GCG GTA CCG ACG GTG                                  60

ACA CTT ACC C                                                            70

(2) INFORMATION FOR SEQ ID NO: 15:

(i) SEQUENCE CHARACTERISTICS:
            (A) LENGTH:        26 base pairs
            (B) TYPE:          nucleic acid
            (C) STRANDEDNESS:  single strand
            (D) TOPOLOGY:      linear (ii) MOLECULE TYPE:

(iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:

(xi) SEQUENCE DESCRIPTION: SEQ ID NO: 15:

GGG TAA GTG TCA CCG TCG GTA CCG CA                                       26

(2) INFORMATION FOR SEQ ID NO: 16:

(i) SEQUENCE CHARACTERISTICS:
            (A) LENGTH:        44 base pairs
            (B) TYPE:          nucleic acid
            (C) STRANDEDNESS:  double strand
            (D) TOPOLOGY:      linear (ii) MOLECULE TYPE:

(iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
```

```
        (F) TISSUE TYPE:
        (G) CELL TYPE:
        (H) CELL LINE:
        (I) ORGANELLE:

(vii) IMMEDIATE SOURCE:

(xi) SEQUENCE DESCRIPTION: SEQ ID NO: 16:

AAA TCT GGT CCG TGC TGA ATT CAA AGC TTG                               30

AAG AAG GTG AAT TC                                                    44

(2) INFORMATION FOR SEQ ID NO:  17:

(i) SEQUENCE CHARACTERISTICS:
         (A) LENGTH:       24 base pairs
         (B) TYPE:         nucleic acid
         (C) STRANDEDNESS: double strand
         (D) TOPOLOGY:     linear (ii) MOLECULE TYPE:

(iii) HYPOTHETICAL:

(iv) ANTI-SENSE:

(v) FRAGMENT TYPE:

(vi) ORIGINAL SOURCE:
         (A) ORGANISM:
         (B) STRAIN:
         (C) INDIVIDUAL ISOLATE:
         (D) DEVELOPMENTAL STAGE:
         (E) HAPLOTYPE:
         (F) TISSUE TYPE:
         (G) CELL TYPE:
         (H) CELL LINE:
         (I) ORGANELLE:

(vii) IMMEDIATE SOURCE:

(xi) SEQUENCE DESCRIPTION: SEQ ID NO: 17:

TGC TAC AAC GAA CTG AAC GGT TGC                                       24

(2) INFORMATION FOR SEQ ID NO:  18:

(i) SEQUENCE CHARACTERISTICS:
         (A) LENGTH:       39 base pairs
         (B) TYPE:         nucleic acid
         (C) STRANDEDNESS: double strand
         (D) TOPOLOGY:     linear (ii) MOLECULE TYPE:

(iii) HYPOTHETICAL:

(iv) ANTI-SENSE:

(v) FRAGMENT TYPE:

(vi) ORIGINAL SOURCE:
         (A) ORGANISM:
         (B) STRAIN:
         (C) INDIVIDUAL ISOLATE:
         (D) DEVELOPMENTAL STAGE:
         (E) HAPLOTYPE:
         (F) TISSUE TYPE:
         (G) CELL TYPE:
         (H) CELL LINE:
         (I) ORGANELLE:

(vii) IMMEDIATE SOURCE:

(xi) SEQUENCE DESCRIPTION: SEQ ID NO: 18:

AAA TCT GGT CCG TGC TGA ATT CAT GAA GAA                               30
```

GGT GAA TTC                                                                                   39

(2) INFORMATION FOR SEQ ID NO: 19:

(i) SEQUENCE CHARACTERISTICS:
        (A) LENGTH:        24 base pairs
        (B) TYPE:          nucleic acid
        (C) STRANDEDNESS:  double strand
        (D) TOPOLOGY:      linear (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:

(xi) SEQUENCE DESCRIPTION: SEQ ID NO: 19:

TGC TAC AAC GAG CTC AAC GGT TGC                                                               24

(2) INFORMATION FOR SEQ ID NO: 20:

(i) SEQUENCE CHARACTERISTICS:
        (A) LENGTH:        39 base pairs
        (B) TYPE:          nucleic acid
        (C) STRANDEDNESS:  double strand
        (D) TOPOLOGY:      linear (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:

(xi) SEQUENCE DESCRIPTION: SEQ ID NO: 20:

AAA TCT GGT CCG TGC TGA ATT CAT GAA GAA                                                       30

GGT GAA TCC                                                                                   39

(2) INFORMATION FOR SEQ ID NO: 21:

(i) SEQUENCE CHARACTERISTICS:
        (A) LENGTH:        458 base pairs
        (B) TYPE:          nucleic acid
        (C) STRANDEDNESS:  single strand (D) TOPOLOGY:     linear (ii) MOLECULE TYPE:

(iii) HYPOTHETICAL:

(iv) ANTI-SENSE:

(v) FRAGMENT TYPE:

(vi) ORIGINAL SOURCE:
         (A) ORGANISM:
         (B) STRAIN:
         (C) INDIVIDUAL ISOLATE:
         (D) DEVELOPMENTAL STAGE:
         (E) HAPLOTYPE:
         (F) TISSUE TYPE:
         (G) CELL TYPE:
         (H) CELL LINE:
         (I) ORGANELLE:

(vii) IMMEDIATE SOURCE:

(xi) SEQUENCE DESCRIPTION: SEQ ID NO: 21:

```
TGATACGAAA CGAAGCATTG GAATTCTACA ACTTGCTTGG                    40

ATTCCTACAA AGAAGCAGCA ATTTTCAGTG TCAGAAGTCG                    80

ACCAAGGAGG TCTAGATAAC GAGGGCAAAA A                            111

ATG AAA AAG ACA GCT ATC GCG ATT GCA GTG GCA                   144
Met Lys Lys Thr Ala Ilo Ala Ilo Ala Val Ala
 1               5                  10

CTG GCT GGT TTC GCT ACC GTA GCG CAG GCC GAC                   177
Leu Ala Gly Phe Ala Thr Val Ala Gln Ala Asp
            15                  20

TCT CTG GGT CGT GAA GCT AAA TGC TAC AAC GAG                   210
Ser Leu Gly Arg Glu Ala Lys Cys Tyr Asn Glu
        25                  30

CTC AAC GGT TGC ACT AAG ATC TAC GAC CCG GTT                   243
Leu Asn Gly Cys Thr Lys Ile LIE Tyr Asp Pro Val
    35                  40

TGC GGT ACC GAC GGC AAC ACT TAC CCG AAC GAA                   276
Cys Gly Thr Asp Gly Asn Thr Tyr Pro Asn Gly
45                  50                  55

TGC GTT CTG TGC TTC GAA AAC CGT AAA CGT CAG                   309
Lys Val Leu Cys Phe Gly Asn Arg Lys Arg Gln
                60                  65

ACT TCT ATC CTG ATC CAG AAA TCT GGT CCG TGC                   342
Thr Ser Lie Leu Lie Gln Lys Ser Gly Pro Cys
            70                  75

TTA ATT CAT GAA GAA GGT GAA TTC TCA GAA GCT                   375
Leu Lie His Glu Glu Gly Glu Phe Ser Glu Ala
            80                  85

CGC GAA GAT ATC AGA GCT GAA ACT GTT GAA AGT                   408
Arg Glu Asp Lie Arg Ala Glu Thr Val Glu Ser
        90                  95

TGT TTA NNN CGT AAT AAG GAG TCT                               432
Cys Leu Arg Asn Lys Glu Ser
100             105

TAATGACTCT AGAGGTCGAA ATTCAC                                  458
```

1

PHAGEMIDS AND PROCESS OF PREPARATION

This application is a continuation of application Ser. No. 08/458,669, filed Jun. 02, 1995, now abandoned.

BACKGROUND OF THE INVENTION

1. Field of the Invention

The invention relates to immunology and more particularly to phagemids.

2. Brief Description of Related Art

Experimental systems have been developed which mimic or directly use the broad repertoire of structures generated in natural production of antibodies. This has been extended by the introduction of additional combinatorial components by mixing of light and heavy immunoglobulin chains and by taking naive repertoires (e. g. IgM) which contain also variants which would normally have been eliminated since they cross-react with endogenes antigenes.

Further, a directed evolution of a protein has been described by selecting mutant neutrophil elastase inhibitors displayed on M13 fusion phages Roberts B. L., Markland W., Ley A. C., Kent R. B., White D. W. Guterman S. K. and Ladner R. C. (1992) Directed evolution of a protein: selection of potent neutrophil elastase inhibitors displayed on M13 fusion phage. Proc. Natl. Acad. Sci. USA 89, 2429–2433. The stability of this known system is, however, critical. An object of the present invention is to select ligands directed towards compact target sites which must be regarded as a complementary alternative to known systems which use larger molecules in which the variable regions are spread over larger areas.

SUMMARY OF THE INVENTION

According to one embodiment, the problem underlying the invention has been solved by a collection of phagemids comprising

- a promotor
- a gene coding for a fusion between a ligand protein, wherein the ligand protein in its processed state would comprise of from 40 to 60 amino acid residues, and a filamentous single strand DNA bacteriophage protein,
- at least one transcription terminator sequence
- a replication origin derived from a filamentous single strand DNA bacteriophage,
- a plasmid replication origin and
- facultatively at least one selection marker.

According to a preferred embodiment, the lambda $P_L$-promotor is used for the phagemids.

Preferably, the ligand protein is a variant of the human pancreatic secretory trypsin inhibitor (hPSTI) or the bovine pancreatic trypsin inhibitor (bPTI).

As regards hPSTI and bPTI, reference is made to the following prior art.

hPSTI: British Patent Specification GB-A-8 700 204.

bPTI: Markland et al. in Gene, 109 (1991) 13–19 and Marks et al. in J. Biol. Chem., 261 (1986) 7115–7118.

The ligand protein can be a variant of hPSTI randomized in the trypsin-inhibitory loop, especially randomized in the region of amino acid 17 to 23.

According to another embodiment of the invention a collection of *Escherichia coli* clones or cells is provided representing a collection of phagemids according to the invention wherein the phagemids are carried in plasmid form.

Preferably, the clones or cells of *Escherichia coli* belong to a strain comprising a lambda-repressor, such as *Escherichia coli* WK6 and especially *Escherichia coli* WK6 (lambda)mutS.

According to another embodiment of the invention a collection of phagemids particles is provided, wherein the phagemid particles are produced from a collection of *Escherichia coli* clones or cells according to the invention.

According to a further embodiment of the invention a process for isolating phagemid particles with strong binding characteristics for a defined target molecule is provided, wherein the process is characterized in that (a) a collection of phagemid particles according to the invention is subjected in the presence of the target molecule to an affinity enrichment method in a manner known per se, (b) a sub-collection of strongly binding phagemid particles is amplified by means of *Escherichia coli* in a manner known per se, (c) facultatively steps (a) and (b) are repeated and (d) one or a few phagemid particles which exhibit strong binding characteristics for the target molecule, are separated.

According to another embodiment of the invention, phagemid particles are provided which exhibit strong binding characteristics for a defined target molecule, wherein the phagemid particles are obtained according to the process of the invention. Preferred are phagemid particles which exhibit strong binding characteristics for a protease as defined target molecule, such as alpha-chymotrypsin or elastase.

Finally, according to another embodiment to the invention purified ligand proteins are provided which can be derived from phagemid particles according to the invention and prepared free of bacteriophage protein, such as bacteriophage pIII protein, by proteolytic cleavage of the hybrid protein, introduction of a stop codon between the coding region for the ligand protein and the coding region for the bacteriophage protein, such as bacteriophage pIII protein, or subcloning the ligand protein gene or parts of it into another expression vector.

As regards a better understanding of the invention, the following glossary is given.

Phagemid and phasmid: These terms are identical.

Filamentous single strand bacteriophage: M13, fd and f1 are examples of single strand bacteriophage which differ from each other in only a few base mutations and can be considered to all intents and purposes as interchangeable.

Superinfection: A superinfection with a bacteriophage consists of addition of a bacteriophage to a bacterial culture already carrying phagemids. On infecting the cell, the bacteriophage supplies the functions required for single strand replication and the coat proteins required for packaging the single strand DNA products, these particles being secreted into the medium. The cultures do not lyse during this process so that both bacterial clones on the one hand and bacteriophage and phagemid particles on the other hand can be isolated from the same culture.

Ligand: This term refers to a molecule which can bind specifically to a defined target molecule. In the context of the invention the ligand is presented on the surface of phagemid particles. By randomly mutating the gene for the ligand at a specific site a large library of ligand variants is produced.

Panning: Panning is defined as a process of allowing phagemids to adsorb to a surface coated with a target molecule, including subsequent washing and specific elution of a strongly binding phagemid, for example by addition of mild acid.

A phagemid is defined as a bacterial plasmid which contains in addition to the plasmid replication origin, a second origin of replication derived from a single-strand bacteriophage. Cells carrying such a phagemid can, on superinfection with a helper bacteriophage, such as M13 or a derivative thereof, also replicate via the single strand replication modus. This results in single strand phagemid DNA being packaged into infectious particles coated by bacteriophage coat proteins. Phagemid DNA can thus be established in (i) stable bacterial clones carrying double stranded DNA in plasmid form or (ii) as bacteriophage-like particles from the supernatants of superinfected cultures. The latter can inject their DNA into Escherichia coli strains carrying the F-sex pilus (as a known precondition for infections), in which they reestablish themselves as plasmids. The special feature of phagemids which can be used for a presentation of particular products, viz. ligands, is the presence of a gene on the phagemids which consists of a fusion between the gene for the product to be presented and a bacteriophage coat protein gene. An example for such a bacteriophage coat protein gene is gpIII, the gene for the coat protein III (pIII) of phages M13 or fd. This results, on superinfection with an M13-like phage in the production of phagemid particles in the supernatant where the ligand is physically coupled via the bacteriophage coat protein to the gene which encodes the ligand. By randomly mutagenizing the ligand gene at a specific site, the invention in question provides a library of phagemids containing tens of millions of ligand variants. The concept of the present invention is that some of these variant ligands will have specific binding affinities for a particular target molecule. The subset of strongly binding phagemids can be selected by, for example, binding on a surface coated with the target molecule, the poorly binding majority of phagemids being washed away. The specific strongly-binding population is then eluted by, for example, weak acid. This enriched subpopulation of phagemids can then be amplified by reinfection and cultivation in Escherichia coli. Successive rounds of such binding and amplification lead to the enrichment of a few variant ligands which exhibit strong specific binding characteristics for the target molecule.

In other words, molecular repertoires containing tens of millions of mutant products can be produced in a form which allows a physical adsorption-based simultaneous selection of gene and gene product. Repeated cycles of selection and amplification allow the enrichment for novel proteins with high affinity for particular target molecules. The basis for the coupling of gene and gene-product is the use of the single-strand bacteriophage propagation system in which plasmids containing the origin of replication of the single-strand phage (phagemids) can be packed into a phage-protein-coated particle on superinfection by a helper phage. The phagemid can encode a gene product which consists of a fusion between one of the phage coat proteins and a second component which will then be presented on the surface of the particle in which the phagemid is packed.

BRIEF DESCRIPTION OF THE DRAWINGS

In the following, the invention is more precisely described by reference to FIGS. 1A–1C to 5 and experimental data.

FIGURE LEGENDS

FIG. 1(a) Generation of pSKAN8. The phagemid pMAMPF3-PSTI4 large HindIII-XbaI(partialXbaI) fragment was ligated to the small HindIII-XbaI fragment of plasmid pSEX40 (Breitling et al., A surface expression vector for antibody screening. Gene 104, 147–153 1991) which contains a linker region with the YOL-antigen "tag", and the pIII coding region deleted for the pIII-leader. Cleavage of pANDRE-13 with HindIII, removal of the cohesive ends with S1-nuclease and religation yielded a deletion product, pANDRE13-4, in which the PSTI and pIII genes are in frame. Mutations were introduced at two positions to create the vector pSKAN8, namely the mutation of the stop codon at the end of the PSTI coding sequence (TGAATT-SEQ. ID. NO: 1>TTAATT SEQ. ID. NO: 2) and the creation of a SacI-cleavage site 5'- to the planned hypervariable site within the PSTI coding region (AACGAACTGAAC SEQ. ID. NO: 3->AACGAGCTCAAC SEQ. ID. NO: 4). A 205 bp PCR reaction product created in the presence of primers # 533 and # 528 on ss pANDRE13-4 template was cleaved with SalI and SacI to yield a 132 bp fragment (F1). Similarly a 224 bp fragment was created by PCR on ss pANDRE13-4 template using primers # 1255 and # 529. This was cleaved with SacI and EcoRV (F2). The fragments F1 and F2 were ligated into SalI-EcoRV cleaved pANDRE13-4. The resulting plasmid was designated pANDRE13-7. The stop codon was removed as follows: a PCR amplification was set up on <1 pMole ss pANDRE13-4 with the mutational primer # 1243 (15 pmole), 5' primer # 529 (20 pmole) and the 3' primer # 1255 (10 pmole). The principle 225 bp product was cleaved with SacI and EcoRV to yield a 174 bp fragment which was inserted into SacI-EcoRV cleaved pANDRE13-7 and transformed into E. coli WK6(Lambda)mutS an F+strain (Dower et al., high efficiency transformation of E. coli by high voltage electroporation. Nucleic Acids Res. 16, 6127–6145; 1988). Bacteriophage and packaged phagemid preparations were carried out as described (Smith and Scott, libraries of peptides and proteins displayed on filamentous phage. Meth. Enz. 217, 228–257, 1992). Primer deoxyribonucleotides:

\# 1243 CTGAGAATTCACCTTCTTCATGAAT-TAAGCACGGACC; SEQ. ID. NO: 5
\# 526 CATGAATTCCGCACGGACC; SEQ. ID. NO: 6
\# 527 GGTCCGTGCGGAATTCATG; SEQ. ID. NO: 7
\# 528*CCGTTGAGCTCGTTGTAGCATTTAGCT-TCACG; SEQ. ID. NO: 8
\# 533 GCATTGGAATTCTACAACTTGC; SEQ. ID. NO: 9
\# 1255 GGGATTTTGCTAAACAAC. SEQ. ID. NO: 10

FIG. 1(b). Sequences [SEQUENCE ID NOS: 16–20, respectively] modified during pSKAN8 construction.

Figure 1C:
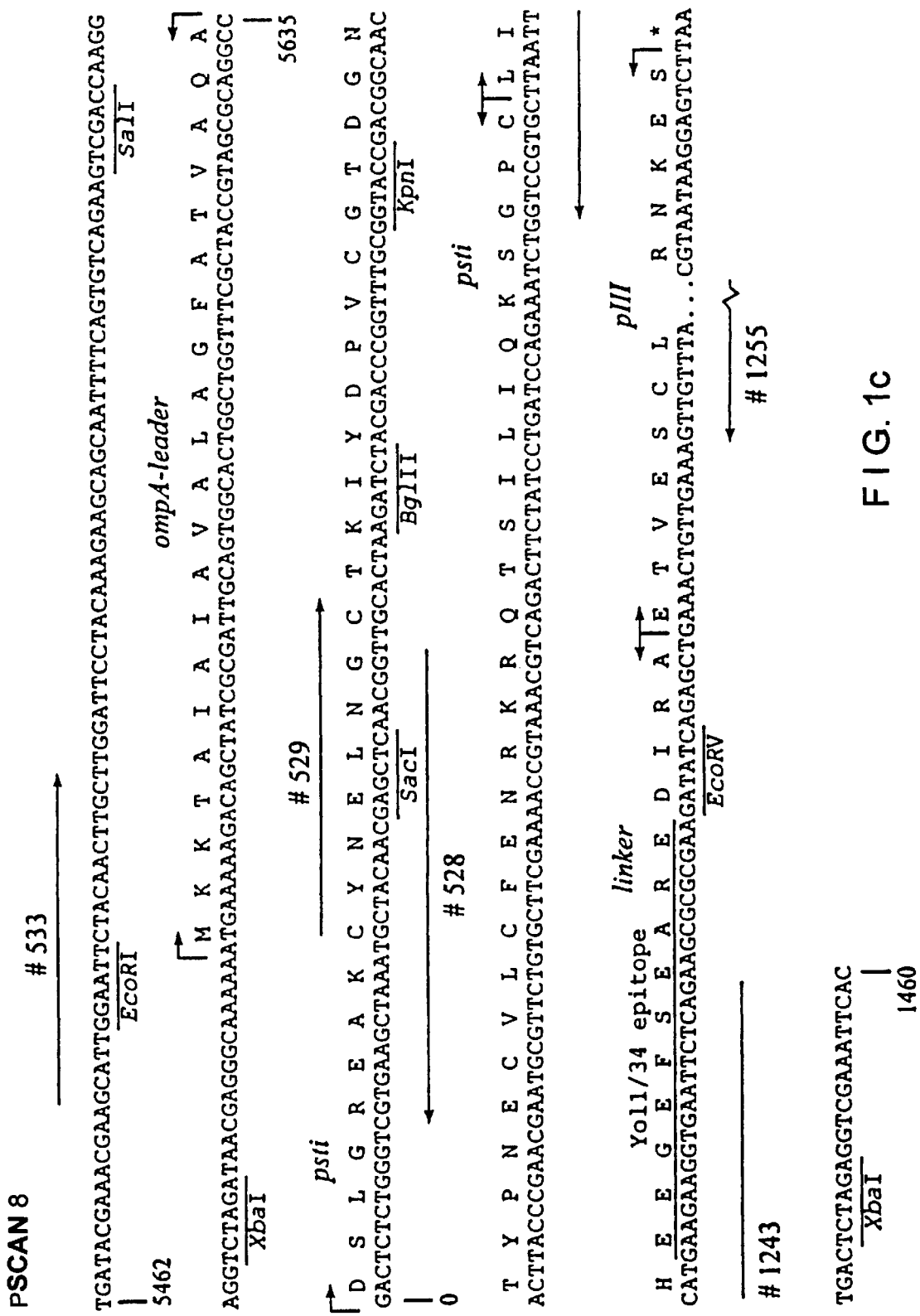

FIG. 1(c). Significant features of the pSKAN8 sequence [SEQ. ID. NO: 21]. Primer binding sites are indicated.

Figure 2:
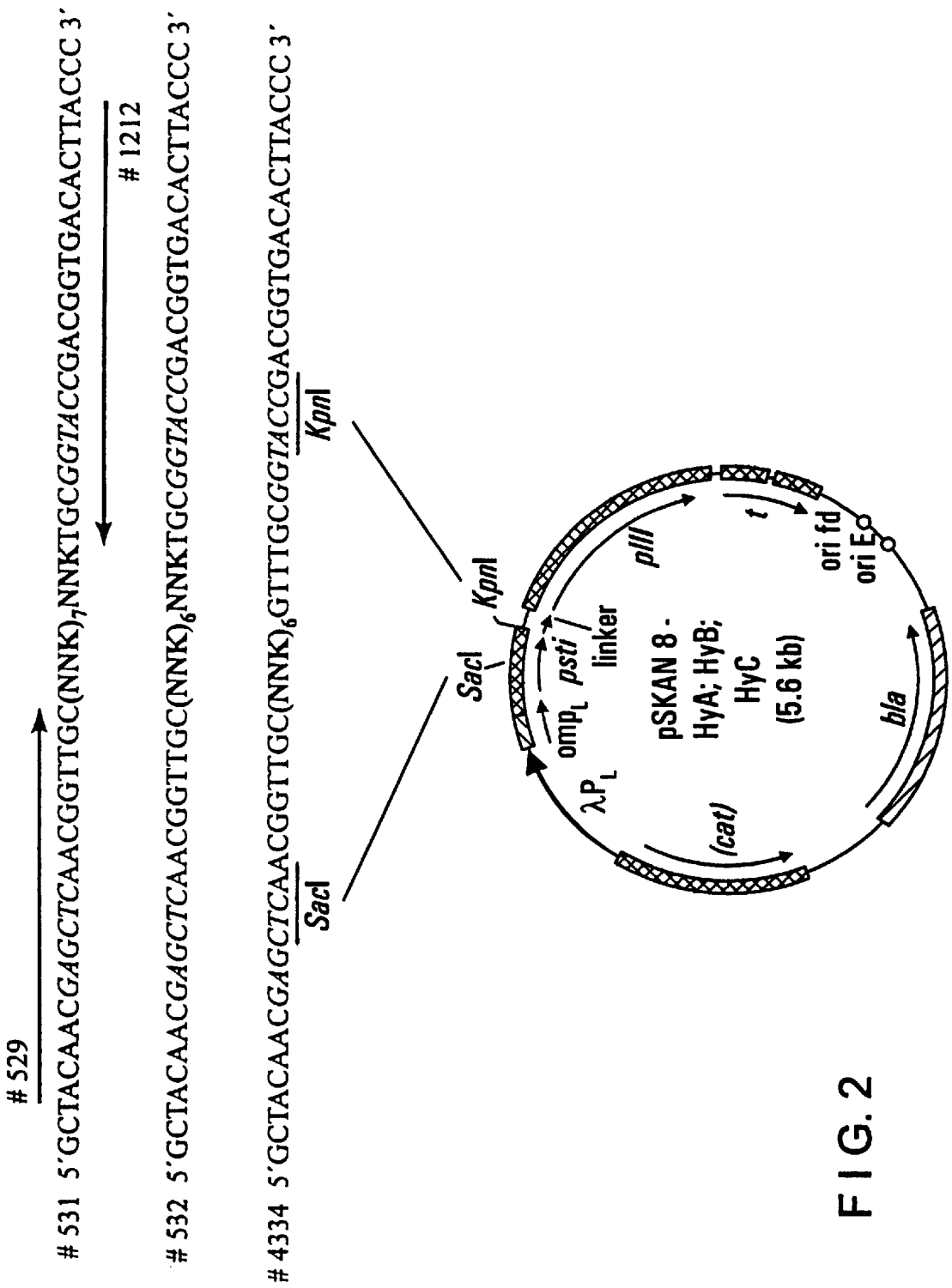

FIG. 2. Three sets of hypervariable cassettes, to replace the SacI-KpnI region, were created by limited PCR amplification (5 cycles): Oligonucleotides # 531, # 532 or # 4334, SEQ. ID NOS: 12, 13 and 14, respectively (1 pmole each) in 20 µl for respectively bank HyA, HyB and HyC were amplified with with primers # 529 and # 1212 (each 20 pmole). Subsequent cleavage of the PCR reaction products with SacI and KpnI allowed insertion into pSKAN8, with vector (3 pmole) and cassette (10 pmole) in 50 µl ligation mix. Native vector sequences were selectively removed by a BglII cleavage (see FIG. 1 (c)) of the ligation mixtures after a phenol/chloroform/ethanol extraction to remove ligase. Transformations were carried out with small aliquots by electroporation into Escherichia coli WK6(Lambda) mutS. The clones were plated on ampicillin LB plates and dilution controls counted. The yields were $1.0\ (+/-0.43) \times 10^6$ pro pmole DNA, totalling $8.38 \times 10^6$ clones for pSKAN8-HyA, $1.57 \times 10^7$ clones for pSKAN8-HyB and yielding a total of 7×10⁶ clones for pSKAN8-HyC i.e. a total from all three banks of 3.11×10⁷ clones.

Oligonucleotides used: # 529 GCTACAACGAGCT-CAACGGTTGC; SEQ. ID. NO: 11 # 531 GCTACAACGAGCTCAACGGTTGC(NNK)₇NNKTGCGGTACCGACGGTGACACTTACCC; SEQ. ID. NO: 12 # 532 GCTACAACGAGCTCAACGGTTGC(NNK)₆NNKTGCGGTACCGACGGTGACACTTACCC; SEQ. ID. NO: 13 # 4334 GCTACAACGAGCTCAACGGTTGC(NNK)₆GTTTGCGGTACCGACGGTGACACTTACCC; SEQ. ID. NO: 14 # 1212 GGGTAAGTGTCACCGTCGGTACCGCA, where SEQ. ID. NO: 15 N=A, C, G or T; K=T or G (allowing tryptophan and methionine codons but reducing the probability of a stop-codon to 33% of the original value i.e. final probability of a stopcodon should be 1 in 64 codons or ca. 1 in 9 of the variant genes). SacI and KpnI sites are underlined.

Figure 3:
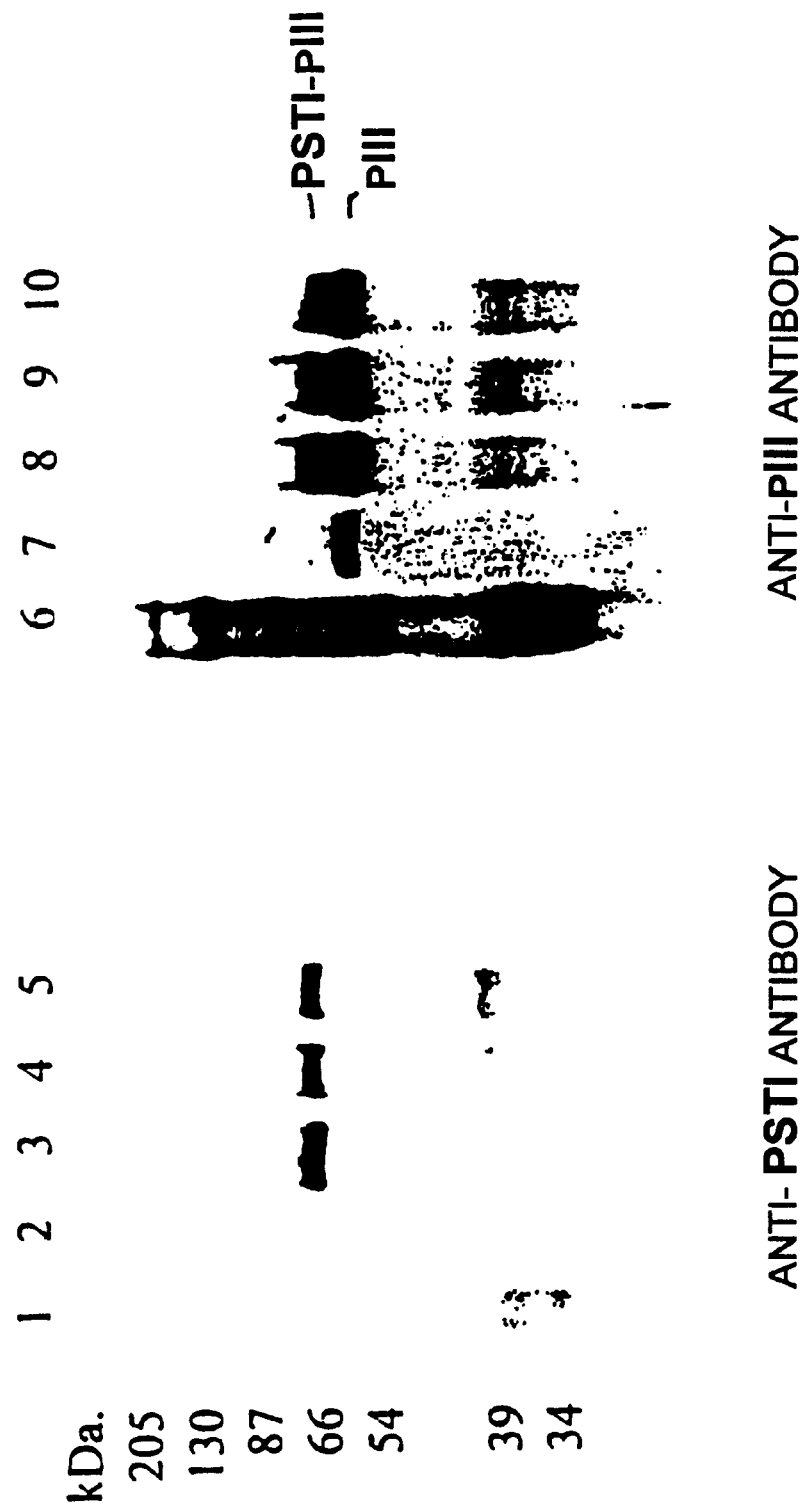

FIG. 3. Western blots of phage preparations showing pIII and hPSTI-pIII fusion proteins. Lanes: 1+6, prestained molecular weight marker; 2+7, M13K07 phage; 3+8, pSKAN8 phagemid; 4+9, HyA phagemid and 5+10, HyB phagemid. Phagemid were packaged from *E. coli* cells using M13K07 helper-phage. Resulting phage particles were collected by PEG-precipitation. Phage proteins were separated by SDS-PAGE (10% T; 3% C gels) according to Schägger and Jagow (Tricine-sodium dodecyl sulfate-polyacrylamide gel electrophoresis for the separation of proteins in the range from 1 to 10 kDa. Anal. Biochem. 166, 368–379 (1987) and transferred onto nitrocellulose. The left blot was incubated with monospecific anti-PSTI rabbit serum (a gift from Diagnostic Research, Fa. Merck), the right blot with a monoclonal antibody directed against pIII. Proteins were stained with peroxidase labeled secondary antibodies (Biorad).

FIG. 4. Amino acid distribution within the hypervariable regions of banks HyA and HyB. The aa distribution was calculated from the data in Tabel 1. Calculated frequencies are compared with aa frequencies expected for a random distribution of nucleotides at positions 1 and 2, and a 1:1 distribution of G and T at the third position of each codon.

Figure 5:
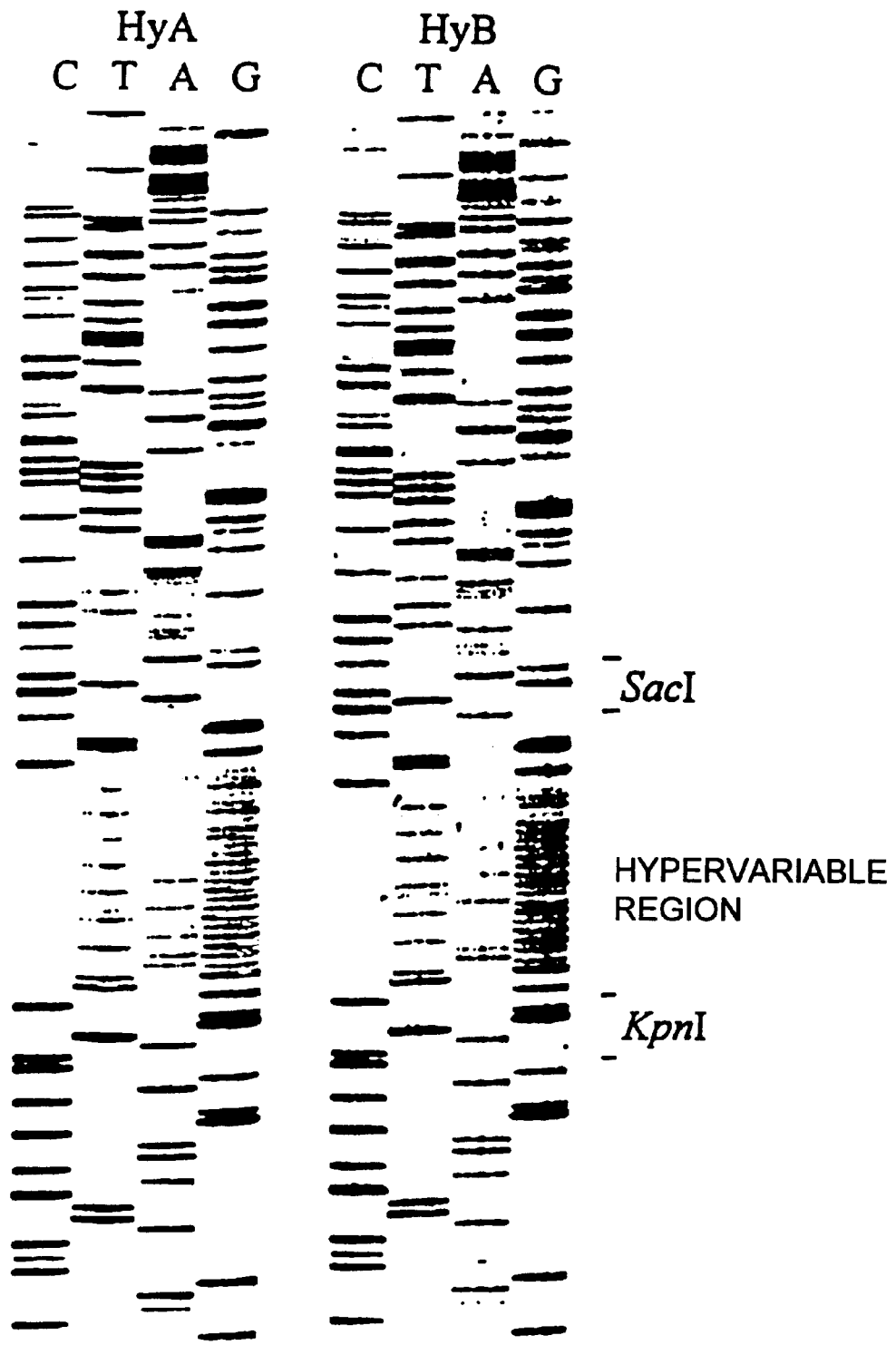

FIG. 5. Sequencing of total banks HyA and HyB. An aliquot of *E. coli* cells from each bank was used as inoculum and superinfected with M13K07 helper phages. Phagemid DNA was purified by PEG-precipitation and phenol extraction (Smith and Scott, 1992) and sequenced (as a pool) with primer # 1255 (FIG. 1c) according to Sanger et al. (1977). The autoradiogram represents the coding strand (5' to 3' direction from top to bottom) showing the pattern (NNG/T)₈ and (NNG/T)₇ within the hypervariable regions.

| pSKAN8-HyA | | | pSKAN8-HyB | | |
|---|---|---|---|---|---|
| 1st base | 2nd base | 3rd base | 1st base | 2nd base | 3rd base |
| G: 0.420 | 0.350 | 0.595 | 0.363 | 0.331 | 0.610 |
| A: 0.245 | 0.325 | 0.025 | 0.338 | 0.299 | 0.000 |
| T: 0.180 | 0.165 | 0.375 | 0.130 | 0.143 | 0.383 |
| C: 0.155 | 0.160 | 0.005 | 0.169 | 0.227 | 0.007 |

Table 1. Nucleotide distribution within the hypervariable regions of banks HyA and HyB.

Phagemid DNA from random single clones of each bank was sequenced according to Sanger et al. (1977). Sequencing data from 25 clones (200 codons) of bank HyA and 22 clones (154 codons) of bank HyB were taken into account.

A phagemid pSKAN8 was created which contains a fusion between the human pancreatic secretory trypsin inhibitor gene and the M13 pIII protein gene. Cassettes containing the sequences (NNT/G)₇ or (NNT/G)₈ were used to randomize the amino acid coding region in the trypsin-inhibitory loop (amino acids 17 to 23) of hPSTI. Some over 10 million individual clones were generated in a mutS *Escherichia coli* strain, thus creating the phagemid banks designated pSKAN8-HyA and pSKAN8-HyB, respectively. It was estimated that the hybrid protein, i. e. PSTI-variant-pIII, was represented statistically at a frequency of one to two molecules per phagemid particle, i. e. one third of the total pIII protein in the particles.

Thus, a phagemid was constructed which contains a hybrid gene encoding the physically well characterized human pancreatic secretory trypsin inhibitor (hPSTI), a compact 56 amino-acid protein, fused to the pIII gene of bacteriophage M13. This phagemid can be propagated as double stranded plasmid DNA or on infection with single-stranded helper phage, packaged as plus-strand single stranded DNA.

The correct folding and presentation of the hybrid protein on the particles were tested by specific adsorption on immobilised trypsin (the unmutated pSKAN8) as well as panning on immobilized anti-PSTI antiserum.

Selection for variants binding strongly to alpha-chymotrypsin as a target molecule yielded four novel specific chymotrypsin inhibitors. This demonstrates the general functionality and applicability of the system.

Compared to, say, immunoglobolin-presentation phagemids, bPTI or hPSTI will have the advantage, for particular applications, that the epitope bound will be relatively small thus allowing targetting of shorter conserved regions, particularly those partially concealed as in membrane receptors;

the production of antigenic components of vaccines in which only the mutated region should be antigenic is conceivable, the majority of the protein being a correctly folded human protein without posttranslational modification sites.

Banks according to the invention represent a combined mutational density and diversity of a short region in excess of that present in similar banks. An antibody bank of 10⁷ variants contains, for example, only some tens to a hundred or so different mutant variants for each CDR-loop. In the case of the small target, i. e. where 5 or 6 amino acid interactions may be involved over a linear crossection of say 30 or 40 Angstrom, the likelyhood of selecting a specific ligand from a bank according to the invention should be considerably higher than for other banks. In this respect, the invention is to be considered as complementary to other banks created with the intent of creating specific ligands which recognize a large area on the surface of target molecules.

Materials and Methods

Phenol-chloroform extractions and ethanol precipitations were used to purify the DNA after each PCR, restriction cleavage and ligation. Plasmid DNA was purified preparatively by caesium chloride ethidium bromide ultracentrifugation. Bacteriophage and packaged phagemid preparations were carried out as described.

Primer desoxyribonucleotide:
1 2 4 3
[5'-CTGAGAATTCACCTTCTTCATGAATTAAGCA CGGACC-3'] SEQ. ID. NO: 5

526 [5'-CATGAATTCCGCACGGACC-3'] SEQ. ID. NO: 6
527 [5'-GGTCCGTGCGGAATTCATG-3'] SEQ. ID. NO: 7
528* [5'-CCGTTGAGCTCGTTGTAGCATTTAGCTTCACG-3']
    SEQ. ID. NO: 8
533 [5'-GCATTGGAATTCTACAACTTGC-3'] SEQ. ID. NO: 9
1255 [5'-GGGATTTTGCTAAACAAC-3'] SEQ. ID. NO: 10
    Primer oligos 528, 529, 1243 and 533 were combined in a PCR reaction in ratios as indicated.
    Hypervariable SacI-KpnI-cassettes for synthesis were as follows:
529 [5'-GCTACAACGAGCTCAACGGTTGC-3'] SEQ. ID. NO: 11
531 [5'-GCTACAACGAGCTCAACGGTTGC(NNK)$_8$TGCGGTACCGACGGTGACACTTACCC-3'] SEQ. ID. NO: 12 SacI KpnI
532 [5'-GCTACAACGAGCTCAACGGTTGC(NNK)$_7$TGCGGTACCGACGGTGACACTTACCC-SEQ. ID. NO: 13 3'] SEQ. ID. NO: 15
1212 [3'-ACGCCATGGCTGCCACTGTGAATGGG-5']
    K=thymidine or guanidine (allowing tryptophan and methionine codons but reducing the probability of a stop-codon to 33% of the original value, i. e. final probability of a stop codon should be 1 in 64 codons or 1 in 9 of the variant genes).

Production of the starting vector pSKAN8

The plasmid pMAMPF3-hPSTI (FIG. 1(a)) is an expression plasmid in which the OmpA-leader peptide is fused to the first amino acid of the synthetic human pancreatic secretory trypsin inhibitor hPSTI such that production, secretion and correct cleavage of the leader peptide occurs.

This phagemid was used as donor of the expression system of the hPSTI gene, plasmid replication functions and the M13 phage replication origin (large HindII-XbaI [partial cleavage] fragment). The plasmid pSEX40 (FIG. 1(a)), an expression vector for the M13 pIII gene product was used as donor for the pIII gene (small HindIII-XbaI fragment). The ligation product (FIG. 1(a)) has the hPSTI and pIII genes juxtaposed correctly but still containing a stop codon at the end of the hPSTI gene and with different reading frames which can be united by deletion of the HindIII sticky ends. The resulting plasmid was designated pANDRE-13. Cleavage of pANDRE-13 with HindIII, removal of the cohesive ends with S1-nuclease and religation yielded a deletion product, pANDRE-13-4 (FIGS. 1(a) and 1(b)), in which the hPSTI and pIII genes are in frame. This was confirmed with a Mn$^{++}$-buffer sequencing on the double-stranded DNA using primer 1255.

Mutations had still to be introduced at two positions to create the vector pSKAN8 (FIG. 1(a)) into which hyper-variable cassettes could be inserted, namely the mutation of the stop codon at the end of the hPSTI coding sequence (TGAATT [SEQ. ID. NO: 1]->TTAATT [SEQ. ID. NO: 2]) and the creation of a SacI-cleavage site 5' to the mutation site within the hPSTI coding region (AACGAACTGAAC [SEQ. ID. NO: 3]->AACGAGCTCAAC [SEQ. ID. NO. 4]). A 205 bp PCR reaction product created in the presence of primers 533 and 528 on single-stranded pANDRE-13-4 template was cleaved with SalI and SacI to yield a 132 bp fragment (F1). Similarly a 224 bp fragment was created by PCR on ss pANDRE-13-4 template using primers 1255 and 529. This was cleaved with SacI and EcoRV (F2). Fragments F1 and F2 were ligated into SalI-EcoRV cleaved pANDRE-13-4. The resulting plasmid, which now contained SacI site at the correct position was designated pANDRE13-7.

To remove the stop codon, the following strategy was used. A PCR amplification was set up on <1 pMol ss pANDRE-13-4 with the mutational primer 1243 (15 pMol), 5' primer 529 (20 pMol) and the 3' primer 1255 (10 pMol). The principle 225 bp product was cleaved with SacI and EcoRV to yield a 174 bp fragment which was cloned into SacI-EcoRV cleaved pANDRE-13-7, transformation being into Escherichia coli WK6(lambda)mutS. The correct product was easily tested for by the absence of a 97 bp EcoRI fragment and confirmed by subsequent sequencing.

Production of the gene banks pSKAN8-HyA and pSKAN8-HyB

The hypervariable cassettes were created by very limited PCR amplification (5 cycles) in two reactions. For bank A, primers 531 (1 pMol), 529 (20 pMol), 1212 (1 pMol) in 20 μl were used. Subsequent cleavage of the PCR reaction products with SacI and KpnI allowed insertion into pSKAN8 to yield the banks pSKAN8-HyA and pSKAN8-HyB, respectively. Native vector sequences were selectively removed by a BglII cleavage of the ligation mixtures after a phenol/chloroform extraction to remove the ligase. Transformations were carried out separately by electroporation into Escherichia coli WK6(lambda)mutS, an F+ strain giving the following yields.

pSKAN8-HyA: 1.0 (sigma=0.43)×10$^6$ pro 5 pMol transformations, totalling 6.5×10$^6$ clones.

pSKAN8-HyB: 0.6 (sigma=0.35)×10$^6$ clones.

The clones were all plated, counted and collected in LB medium plus 10% glycerol and frozen. Aliquots of 1 ml were pooled for each bank, inoculated into 500 ml LB medium with 10$^9$ M13KO7 helper phage. The supernatants were concentrated over a hundredfold with PEG precipitation, pellets washed, resuspended, and further centrifuged as an additional sterilization step. These packaged phagemid suspensions were conserved at 4° C.

References

1. Smith G. P. (1985) Filamentous fusion phage: novel expression vectors that display cloned antigens on the virion surface. *Science* 228, 1315–1317
2. Parmley S. F. and Smith G. P. (1988) Antibody-selectable filamentous fd phage vectors; affinity purification of target genes. *Gene* 73, 305–318
3. Yankovsky N. K., Fonstein M. Y., Lashina S. Y., Bukanov N. O., Yakubovich N. V., Ermakova L. M., Rebentish B. A., Janulaitis A. A. and Debabov V. G. (1989) Phasmids as effective and simple tools for construction and analysis of gene libraries. *Gene* 81, 203–210
4. Bass S., Greene R. and Wells J. A. (1990) Hormone phage; an enrichment method for variant proteins with altered binding properties. *Proteins:Struct.Funct.Genet.* 8, 309–314
5. Devlin J. J., Panganiban L. C. and Devlin P. E. (1990) Random peptide libraries: a source of specific protein binding molecules. *Science* 249, 404–406
6. Szardenings M. and Collins J. (1990) A phasmid optimised for protein design projects: pMAMPF. *Gene* 94, 1–7
7. Tuerk C. and Gold L. (1990) Systematic evolution of ligands by exponential enrichment: RNA ligands to bacteriophage T4 DNA polymerase. *Science* 249, 505–510
8. Breitling F., Dubel S., Seehaus T., Klewinghaus I. and Little M. (1991) A surface expression vector for antibody screening. *Gene* 104, 147–153
9. Clackson T., Hoogenboom H. R., Griffiths A. D. and Winter G. (1991) Making antibody fragments using phage display libraries. *Nature(Lond.)* 352, 624–628
10. Houghten R. A., Pinilla C, Blondelle S. E., Appel J. R., Dooley C. T. and Cuevo J. H. (1991) Generation and use of synthetic peptide combinatorial libraries for basic research and drug discovery. *Nature(Lond.)* 354, 84–86
11. Kang A. S., Barbas C. F., Janda K. D., Benkovic S. J. and Lerner R. A. (1991) Linkage of recognition and replication functions by assembling combinatorial antibody Fab libraries along phage surfaces. *Proc. Natl. Acad. Sci. USA* 88, 4363–4366
12. Lam K. S., Salmon S. E., Hersh E. M., Hruby V. J., Kazmierski W. M. and Knapp R. J. (1991) A new type of synthetic peptide library for identifying ligand-binding activity. *Nature(Lond.)* 354, 82–84
13. Markland W., Roberts B. L., Saxena M. J. and R. C. Ladner S. K. Guterman (1991) Design construction and function of a multicopy display vector using fusions to the major coat protein of bacteriophage M13. *Gene* 109, 13–19
14. Marks J. D., Hoogenboom H. R., Bonnert T. P., McCafferty J., Griffiths A. D. and Winter G. (1991) By-passing immunization. Human antibodies from V-gene librairies displayed on phage. *J. Mol. Biol.* 222, 581–597
15. Smith T. A. and Kohorn B. D. (1991) Direct selection for sequences encoding proteases of known specificity. *Proc. Natl. Acad. Sci. USA* 88, 5159–5162
16. Tsunetsugu-Yokota Y., Tatsumi M., Robert V., Devaux C., Spire B., Chermann J.-C. and Hirsch I. (1991) Expression of an immunogenic region of HIV by a filamentous bacteriophage vector. *Gene* 99, 261–265
17. Venuti M. C.: Molecular genetics and drug discovery. In Friedmann T. [ed.] (1991) *Molecular genetic medicine, Vol.I.* Academic Press, San Diego. pp. 133
18. Brenner S. and Lerner R. A. (1992) Encoded combinatorial chemistry. *Proc. Natl. Acad. Sci. USA* 89, 5381–5383
19. Chiswell D. J. and McCafferty J. (1992) Phage antibodies: will new "coliclonal" antibodies replace monoclonal antibodies?. *TIBTECH* 10, 80–85
20. Dübel S., Breitling F., Seehaus T. and Little M. (1992) Generation of a human IgM expression library in *E.coli. J. Biol. Chem.* 267, 12831–?
21. Gherardi E. and Milstein C. (1992) Original and artificial antibodies. *Nature (London)* 357, 201–202
22. Goldman E. R. and Youvan D. C. (1992) An algorithmically optimized combinatorial library screened by direct imaging spectroscopy. *BioTechnol.* 10, 1557–1561
23. Roberts B. L., Markland W., Ley A. C., Kent R. B., White D. W., Guterman S. K. and Ladner R. C. (1992) Directed evolution of a protein: selection of potent neutrophil elastase inhibitors displayed on M13 fusion phage. *Proc. Natl. Acad. Sci. USA* 89, 2429–2433
24. Barbas III C. F., Rosenblum J. S. and Lerner R. A. (1993) Direct selection of antibodies that coordinate metals from semisynthetic combinatorial libraries. *Proc. Natl. Acad. Sci. USA* 90, 6385–6389
25. Corey D. R., Shin A. K., Yang Q., Janowski B. A. and Craik C. S. (1993) Trypsin display on the surface of bacteriophage. *Gene* 128, 129–134
26. DeGraaf M. E., Miceli R. M., Mott J. E. and Fischer H. D. (1993) Biochemical diversity in a phage display library of random decapeptides. *Gene* 128, 13–17
27. Dübel S., Breitling F., Fuchs P., Braunagel M., Klewinghaus I. and Little M. (1993) A family of vectors for surface display and production of antibodies. *Gene* 128, 97–101
28. Garrard L. J. and Henner D. J. (1993) Selection of an anti-IGF-1 Fab from a Fab phage library created by mutagenesis of multiple CDR loops. *Gene* 128, 103–109
29. Kay B. K., Adey N. B., He Y.-S., Manfredi J. P., Mataragnon A. H. and Fowlkes D. M. (1993) An M13 phage library displaying random 38-amino- acid peptides as a source of novel sequences with affinity to selected targets. *Gene* 128, 59–65
30. Makowski L. (1993) Structural constraints on the display of foreign peptides on filamentous bacteriophages. *Gene* 128, 5–11
31. Matthews D. J. and Wells J. A. (1993) Substrate phage: Selection of Protease substrates by monovalent phage display. *Science* 260, 1113–1117
32. McLafferty M. A., Kent R. B., Ladner R. C. and Markland W. (1993) M13 bacteriophage displaying disulphide-constrained microproteins. *Gene* 128, 29–36
33. Pannekoek H., van Meijer M., Schleef R. R., Loskutoff D. J. and Barbas III C. F. (1993) Functional display of human plasminogen-activator inhibitor-1 (PAI-1) on phages: novel perspectives for structure function analysis by error-prone DNA synthesis. *Gene* 128, 135–140
34. Pinilla C., Appel J. R. and Houghten R. A. (1993) Synthetic peptide combinatorial libraries (SPCLs): identification of the antigenic determinant of β-endorphin recognised by monoclonal antibody 3E7. *Gene* 128, 71–76
35. Smith G. P., Schultz D. A. and Ladbury J. E. (1993) A ribonuclease S- peptide antagonist discovered with a bacteriophage display library. *Gene* 128, 37–42
36. Sönderlind E., Lagerkvist A. C. S., Duenas M., Malmborg A.-C., Ayala M., Danielsson L. and Borrebaeck C. A. K. (1993) Chaperonin assisted phage display of antibody fragments on filamentous bacteriophages. *BioTechnol.* 11, 503–507
37. Willis A. E., Perham R. N. and Wraith D. (1993) Immunological properties of foreign peptides in multiple display on a filamentous bacteriophage. *Gene* 128, 79–83
38. Breitling, F., Dubel, S., Seehaus, T., Klewinghaus, I. and Little, M. (1991) A surface expression vector for antibody screening. *Gene* 104, 147–153.
39. Dower, W. J., Miller, J. F. and Ragsdale, C. W. (1988) High efficiency transformation of *E. coli* by high voltage electroporation. Nucleic Acids Res. 16, 6127–6145
40. Smith, G. P. and Scott, J. K. (1992) Libraries of peptides and proteins displayed on filamentous phage. Meth. Enz. 217, 228–257
41. Schägger, H. and von Jagow, G. (1987) Tricine-sodium dodecyl sulfate-polyacrylamide gel electrophoresis for the separation of proteins in the range from 1 to 10 kDa. Anal. Biochem. 166, 368–379
42. Sanger, F., Nicklen S. and Coulson, A. R. (1977) DNA sequencing with chain-terminating inhibitors. Proc. Natl. Acad. Sci. USA 74, 5463–5467

We claim:

1. A collection of phagemids hosted in an *Escherichia coli* strain comprising a lambda repressor, wherein the phagemids comprise a) a lambda P$_L$-promotor;

b) a gene coding for a fusion between (i) a ligand protein, wherein the ligand protein in its processed state comprises from 40 to 60 amino acid residues and (ii) a filamentous single strand DNA bacteriophage pIII protein;

c) at least one transcription terminator sequence;

d) a replication origin derived from a filamentous single strand DNA bacteriophage;

e) a plasmid replication origin; and facultatively at least one selection marker.

2. A collection of phagemids according to claim 1 wherein the ligand protein has an amino acid sequence corresponding to that of human pancreatic secretory trypsin inhibitor or bovine pancreatic trypsin inhibitor.

3. A collection of phagemids according to claim 1 wherein the ligand protein is a variant of human pancreatic secretory trypsin inhibitor (hPSTI) randomized in the trypsin-inhibitory loop.

4. A collection of *Escherichia coli* clones or cells representing a collection of phagemids according to claim 1, wherein the phagemids are carried in plasmid form.

5. A collection of *Escherichia coli* clones or cells according to claim 1, wherein the clones or cells of *Escherichia coli* belong to a strain comprising a lambda-repressor.

6. A collection of phagemid particles produced from a collection of *Escherichia coli* clones or cells according to claim 1.

7. A process for isolating phagemid particles with strong binding characteristics for a defined target molecule, which comprises;

(a) subjecting a collection of phagemid particles according to claim 1 to an affinity enrichment method in the presence of a target molecule;

(b) amplifying a sub-collection of strongly binding phagemid particles by means of *Escherichia coli;*

(c) repeating facultatively steps (a) and (b); and (d) separating one or a few phagemid particles which exhibit strong binding characteristics for the target molecule.

8. Phagemid particles which exhibit strong binding characteristics for a defined target molecule and obtained according to claim 7.

9. Phagemid particles according to claim 8 which exhibit strong binding characteristics for a protease as a defined target molecule.

10. Purified ligand proteins prepared from phagemid particles according to claim 8 free of bacteriophage protein by one of a) proteolytic cleavage of said particles;

b) introduction of a stop codon between the coding region for the ligand protein and the coding region for the bacteriophage protein comprised by the particles; or c) subcloning a ligand protein gene of the particles or parts of it into another expression vector.

* * * * *